United States Patent [19]

Lämsä

[11] Patent Number: 5,885,946
[45] Date of Patent: Mar. 23, 1999

[54] PROCESS FOR PREPARING A SYNTHETIC ESTER FROM A VEGETABLE OIL

[75] Inventor: Merja Lämsä, Merimasku, Finland

[73] Assignee: Raision Tehtaat Oy Ab, Raisio, Finland

[21] Appl. No.: 793,822

[22] PCT Filed: Sep. 7, 1995

[86] PCT No.: PCT/FI95/00477

§ 371 Date: Mar. 4, 1997

§ 102(e) Date: Mar. 4, 1997

[87] PCT Pub. No.: WO96/07632

PCT Pub. Date: Mar. 14, 1996

[30] Foreign Application Priority Data

Sep. 7, 1994 [FI] Finland ..................... 944118

[51] Int. Cl.⁶ .................. C10M 105/38; C08G 63/78
[52] U.S. Cl. .................. 508/485; 554/167; 554/168; 554/169
[58] Field of Search .................. 554/167, 168, 554/169; 508/485

[56] References Cited

U.S. PATENT DOCUMENTS

| | | | |
|---|---|---|---|
| 2,290,609 | 7/1942 | Goss et al. .................. | 554/167 |
| 2,371,333 | 3/1945 | Johnston .................. | 508/485 |
| 2,469,371 | 5/1949 | Colbeth .................. | 554/167 |
| 3,282,971 | 11/1966 | Metro et al. .................. | 508/485 |
| 3,620,290 | 11/1971 | Kress et al. .................. | 508/485 |
| 3,720,695 | 3/1973 | Meisters .................. | 260/404.8 |
| 4,061,581 | 12/1977 | Leleu et al. .................. | 252/32.7 |
| 4,942,228 | 7/1990 | Gibson .................. | 554/168 |
| 5,043,438 | 8/1991 | Buter .................. | 554/168 |
| 5,071,975 | 12/1991 | Van der Plank et al. .................. | 536/119 |
| 5,116,546 | 5/1992 | Klok et al. .................. | 554/167 |
| 5,648,483 | 7/1997 | Granberg et al. .................. | 554/167 |

FOREIGN PATENT DOCUMENTS

| | | |
|---|---|---|
| 0 349 221 A3 | 1/1990 | European Pat. Off. . |
| 09 391 485 A1 | 10/1990 | European Pat. Off. . |
| 2045817 | 9/1970 | Germany . |
| 4304468 | 8/1994 | Germany . |
| WO 92/00268 | 1/1992 | WIPO . |
| WO 95/22719 | 10/1995 | WIPO . |

OTHER PUBLICATIONS van der Waal, G., et al. Testing, Application, and Future Development of Environmentally Friendly Ester Base Fluids, *Synth. Lubr.* 1993, 10(1), 67–83.

*Primary Examiner*—Jerry D. Johnson
*Attorney, Agent, or Firm*—Pollock, Vande Sande & Amernick

[57] ABSTRACT

The object of the invention is a process for preparing a synthetic ester from a vegetable oil by a two-stage transesterification process. Further objects of the invention are lubricants containing a synthetic ester prepared by the process according to the invention.

11 Claims, No Drawings

PROCESS FOR PREPARING A SYNTHETIC ESTER FROM A VEGETABLE OIL

This application is a 371 of PCT/FI95/00477 filed Sep. 7, 1995.

The objects of the present invention are a process for preparing a synthetic ester from a vegetable oil and lubricants which contain a synthetic ester prepared by said process.

Natural fats and oils have been used as lubricants already for thousands of years. With industrialization mineral based lubricants came also to the market. The applications of lubricants and thus also the requirements set for them have changed and developed with the advance of technology. Various types of synthetic esters and lubricants containing the same have been developed to meet the new requirements.

The purpose of a lubricant is to minimize friction and wear of metals. Lubricants are developed according to the use and they consist of a base fluid and additives improving the lubricative properties. With the development of technology, lubricants are used under more and more severe conditions, such as at very low or very high temperatures (e.g. the turbine engines of aeroplanes). At the same time biodegradability, non-accumulation to the environment, non-toxicity and the use of renewable raw materials have emerged -as new requirements. The use of biodegradable lubricants is of particular importance in the machines and devices used in the fields of agriculture, forestry and building, as the oil used may be left in the environment.

By the synthetic esters developed as lubricants are meant esters prepared from mono-, di- or trialcohols and mono- or dicarboxylic acids by known esterification and transesterification methods. Usually the process comprises combining all the reactants and letting the reaction happen in one stage. The reaction may be carried out in the presence of catalysts, such as acids, bases or metal oxides.

The structure of the synthetic ester used has a profound effect on the stability of the lubricant. Esters decompose by the effect of heat and/or oxygen. It is known to increase the thermal stability of synthetic esters by using in the preparation no beta hydrogen alcohols. Oxidative properties on the other hand can be improved by deuteration of esters.

Synthetic esters intended for a lubricative use are classified by structure as monocarboxylic acid, dicarboxylic acid, polyol and complex esters. Due to their low viscosity and high volatility monoesters are poorly suitable as lubricants. Polyol esters are chemically more stable than for example diesters due to the structure of the polyols used in the preparation of said esters, wherein no hydrogen atom is attached to the $\beta$ carbon atom. Complex esters have promising lubricative properties but the manufacture thereof on an industrial scale is difficult because of the severe conditions required by the reaction, especially if said esters are prepared from purified fatty acids and alcohols.

If polyol esters are prepared by using no alfa hydrogen acids, the stability properties of the esters can be further improved. Metro et al. (CA 859 771) have shown that the no alfa hydrogen carboxylic acids increase the thermal and oxidative stability of esters prepared from no beta hydrogen alcohols, as well as slow down the hydrolysis of the esters.

As the low viscosity polyol esters are not suitable for traditional uses wherein high viscosity is required, it has been aimed at preparing polyol esters of higher viscosity from for example trimethylol propane (TMP). However, it has been found that it is difficult to obtain simple TNT esters with both high viscosity and a low pour point (cf. for example U.S. Pat. No. 4,061,581).

Products based on vegetable oils are nowadays used more and more as lubricants because of their safety to the environment. Natural vegetable and animal oils are glyceride diesters, i.e. tri-, di- or monoesters of glycerol and straight chain saturated and unsaturated fatty acids. The lubricant industry uses for instance rapeseed, rape, soybean, castor, olive, coconut, palm and tall oils.

The advantageous properties of vegetable oils include user friendliness and non-toxicity. In addition to this they degrade in the environment, do not accumulate in the food chain of nature and are renewable raw materials. However, the use of vegetable oils as lubricants has been limited by their poor stability properties. The poor thermal and oxidative stability is due to unsaturated and polyunsaturated fatty acids. On the other hand, the unsatisfactory behaviour of vegetable oils at low temperatures is due to the saturated fraction of fatty acids. By using suitable additives and by favouring in cultivation such varieties which do not have a too high degree of saturation, it has been possible to somewhat improve the stability properties. Also the purification of the oil for technical use is helpful.

Furthermore, attempts have been made to modify natural glyceride esters in order to improve their stability properties. Known processes include catalytic hydrogenation, alcoholysis, geometrical isomerization and sulfurization. For example by hydrogenation a certain amount of double bonds can be removed from the unsaturated part of vegetable oils and by isomerization the amount of undesired isomers can be decreased.

Van der Waal and Kenbeek have presented a process for the preparation of synthetic esters from vegetable oils or animal fats (Proceedings of the Tribology 2000, 8th International Colloqium, Technische Akademie Esslingen, Germany, 14–16 Jun. 1992, Vol II, pp 13.3-1 –13.3-8). The process comprises first decomposing the glyceride esters of the starting material into fatty acids and glycerol and subsequently separating the fatty acid fraction into liquid and solid phases. The fatty acids of the liquid phase are separated by distillation into single fatty acids which can be further modified e.g. by hydrogenation or cracking to obtain the desired raw material. Fractions containing a single fatty acid are esterified with no beta hydrogen polyols for preparing a synthetic ester.

The fatty acids of the ester prepared according to the above described process usually contain less unsaturated double bonds than the fatty acids of the starting material, which improves the oxidative stability. However, the costs of the process are extremely high, due to the multistage separation and purification reactions and the most severe conditions (high pressure and temperature) required by the reaction. Moreover, it has been found that when fractions containing only a single fatty acid are reacted with polyols, plenty of mono- and diglycerides are formed, i.e. all the OH groups of the polyols do not react. This decreases the triglyceride yield and the raw material has to be recycled several times if the yield is to be improved. Furthermore, the reaction of a fatty acid and an alcohol creates water which has to be removed during the reaction.

According to the invention it has now been found that it is possible to prepare synthetic esters with good lubricative properties from vegetable oils by a process which avoids the multistage reaction with several separations and recyclings and by which good yields are obtained.

In the process according to the invention a vegetable oil is first transesterified by reacting the vegetable oil with a lower alkanol to obtain a mixture of fatty acid lower alkyl esters. The process is characterised in that the obtained mixture of esters is further transesterified by reacting the said mixture with a no beta hydrogen polyol of the formula

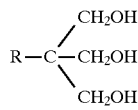

wherein R is a $C_1$–$C_6$ all group, particularly a $C_1$–$C_4$ allyl group, or a —$CH_2OH$ group, and the synthetic ester obtained is recovered.

Vegetable oils suitable as a starting material of the process are for example rapeseed, rape, soybean, castor, olive, coconut, palm, tall, maize, walnut, flaxseed, cotton, sunflower, sesame and almond oils, especially rapeseed oil, rape oil, tall oil and soybean oil, particularly rapeseed oil.

The first transesterification reaction of the process according to the invention is carried out by a process known per se, by reacting a refined or alkalrefined vegetable oil with a lower alkanol to obtain a mixture of fatty acid lower alkyl esters.

The lower alkanol used in the first transesterification reaction is preferably a $C_1$–$C_4$ alkanol, especially methanol or ethanol. The obtained mixture of lower alkyl esters of the vegetable oil is thus preferably a mixture of $C_1$–$C_4$ alkyl esters, especially a mixture of methyl or ethyl esters. If desired, usual esterification catalysts may be used in the reaction, and the amounts of the reactants and the reaction conditions (pressure, temperature, reaction time) are either commonly known or easily chosen by a person skilled in the art.

The first transesterification reaction may be illustrated by the following general reaction scheme I:

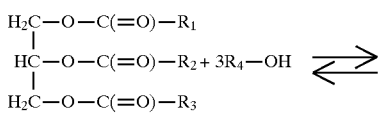 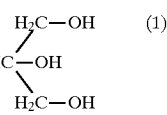

wherein $R_1$, $R_2$ and $R_3$ are fatty acid residues, $R_4$ is an alkyl residue, especially a $C_1$–$C_4$ alkyl residue, and $R_x$ is $R_1$, $R_2$ or $R_3$. Glycerol is formed as a by-product.

The fatty acid lower alkyl ester obtained from the first transesterification reaction is thus a mixture comprising various fatty acids of the vegetable oil used as the starting material. It is typical of the invention that this mixture of fatty acid lower alkyl esters may be used directly as the starting material of the second transesterification reaction without separation or purification of fatty acids.

In the second transesterification reaction according to the invention the mixture of fatty acid lower alkyl esters obtained from the first transesterification reaction is reacted with a no beta hydrogen polyol, such as for example trimethylol ethane, trimethylol propane, trimethylol butane or pentaerythritol, especially with pentaerythritol or trimethylol propane. The conditions required by the reaction are not so severe than those required by the process according to the prior art, and the by-products formed may be present in the reaction.

The second transesterification reaction may be illustrated with the following general reaction scheme II:

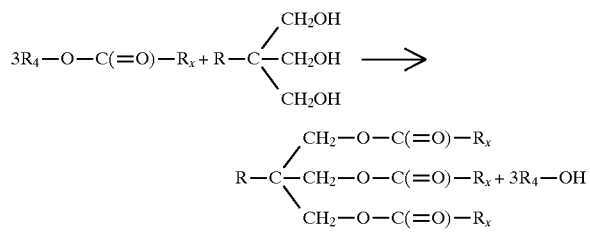

wherein $R_4$ and $R_x$ have the same meanings as in the reaction scheme I and R is a $C_1$–$C_6$ alkyl group, especially a $C_1$–$C_4$ alkyl group, or a —$CH_2OH$ group.

Consequently, it is the question of a totally different chemical reaction than in the process of the prior art wherein a free fatty acid is esterified with an alcohol. In the process according to the invention, an ester is reacted with an alcohol, and thus it is the question of a transesterification reaction which reaction, as well as the reaction conditions required by it and the by-products formed therein, is totally different from the reaction used in the process of the prior art.

The synthetic ester obtained from the second transesterification reaction is recovered and, if desired, purified by conventional methods, for example by neutralization and washing with an aqueous acid. No distillation or any other special treatment is needed as the obtained ester is ready to use as such as a raw material of lubricants.

When a polyol is reacted with a mixture of fatty acid lower alkyl esters, almost all OH-groups of the polyol react into triglycerides. Over 90% of the theoretical yield of the triglyceride is obtained, the proportion of mono- and diglycerides being in total about 10%. The product obtained does not contain any free fatty acids which makes it an especially advantageous raw material for lubricants wherein the oxygenation of free fatty acids would cause problems (corrosion, change of viscosity). The process is well adapted for industrial scale and the synthetic ester obtained has better stability properties than the vegetable oil used as the raw material, while at the same time the advantageous properties of a vegetable oil (biodegradability, non-toxicity, user friendliness) are maintained. By the process it is thus possible to prepare synthetic esters from vegetable oils, for example from rapeseed oil, in a yield of even over 90% of the theoretical.

According to the invention the second transesterification reaction may preferably be carried out in two stages, the reaction temperature of the first stage being from about 50° to about 110° C. and of the second from about 110° to about 160° C. Preferably the reaction temperature of the first stage is from 85° to 100° C. and of the second stage from 110° to 140° C. Reaction time may vary for example from two to twelve hours. Preferably the reaction time of the first stage is about 1 to 7 hours and of the second stage about 1 to 10 hours.

The no beta hydrogen polyol and the mixture of esters are preferably reacted with each other in a molar ratio of about 1:2 to 1:5, especially in the molar ratio of about 1:3,5.

The second transesterification reaction is preferably carried out under reduced pressure, for example under negative pressure of 1.3 to 13 kPa, and optionally in the presence of a catalyst. As catalysts known esterification catalysts, such as acid and base catalysts, for example p-toluene sulfonic acid, phosphoric acid, sodium hydroxide, sodium ethoxide and sodium methoxide, of which sodium hydroxide and sodium methoxide are especially advantageous may be mentioned.

The synthetic ester prepared by the process according to the invention is an excellent raw material for the preparation of lubricants. Lubricants, especially hydraulic oils, which contain a synthetic ester prepared by the process of the invention, optionally with one more additives, are also included in the scope of the invention. As additives for example oxidation inhibitors, antiwear agents, antifoam agents, corrosion inhibitors, dispersants, viscosity index improvers and/or pour point depressers which are generally known in the art, may be used.

Oxidation inhibitors include for example amines and phenols. As antiwear agents and corrosion inhibitors for example phosphates or sulfonates and as antifoam agents for example metal sulfonates, metal phenates, polyesters or silicones may be used. Viscosity index improvers include for example polyisobutenes, styrene-butadiene and ethene-propene-copolymers which all are thus suitable also as pour point depressers.

In the following the invention is further described by means of examples, the purpose of which is to illustrate but not to limit the invention.

EXAMPLE 1
Preparation of a methyl ester of rapeseed oil

Rapeseed oil (0.3 moles) was weighed into a three-necked flask provided with a thermometer, cooler and a stilling device. Sting was started and methanol (2.0 moles) was added. The reaction mixture was heated to 60° C. and the alkali catalyst used was added (0.5% by weight). Stirring was continued for three hours. The progress of the reaction was followed by thin layer chromatography. The reaction mixture was washed with an aqueous acid. The glycerol created in the reaction mixture which as a heavier component settles on the bottom of the vessel was separated and the product mixture was analyzed. Rapeseed oil ester content was 97%.

EXAMPLE 2
Preparation of a synthetic ester from rapeseed oil methyl ester

The methyl ester of rapeseed oil (0.65 moles) was weighed into a three-necked flask provided with a thermometer, a cooler, a stirring device and a reduced pressure generator. The weighed rapeseed oil ester was heated to 50°–110° C., after which trimethylol propane (TMP, 0.19 moles) was added in small proportions with proper stirring. After the alcohol was well mixed, sodium hydroxide used as a catalyst was added (0.1–1.0% by weight of the reaction mixture). Then the reaction mixture was heated under reduced pressure (about 8 kPa) until it started boiling. The reduced pressure was maintained during the whole reaction. The mixture was allowed to boil at the lower temperature (50°–110° C.) for 1 to 7 hours and at the higher temperature (110°–160° C.) for 1 to 10 hours. The progress of the reaction was followed by thin layer chromatography and quantitative IR spectrum. At the end of the reaction the product mixture was neutralized and washed with an aqueous acid, filtrated and washed with water. Drying was performed with anhydrous sodium sulfate. A liquid chromatogram and an IR spectrum were run of the final product. The yield was 90.5% of the theoretical.

EXAMPLE 3
Preparation of an ethyl ester of soybean oil

Soybean oil (0.2 moles) was weighed into a three-necked flask provided with a thermometer, a cooler and a stirring device. Stirring was started and ethanol (1.5 moles) was added. The reaction mixture was heated to 80° C. and the alkali catalyst used (0.4% by weight) was added. Stirring was continued for two hours. The progress of the reaction was followed by thin layer chromatography. The reaction mixture was washed with an aqueous acid. Glycerol was separated from the reaction mixture and the product mixture was analyzed by liquid chromatography. Soybean oil ester content was 96%.

EXAMPLE 4
Preparation of a synthetic ester from soybean oil ethyl ester

Soybean oil ethyl ester (0.7 moles) was weighed into a three-necked flask provided with a thermometer, a cooler, a stirring device and a reduced pressure generator. After the weighed ester was heated to 50°–110 C., trimethylol ethane (TME, 0.2 moles) was added in small proportions with proper stirring. When the alcohol was well mixed, the catalyst used (sodium hydroxide, 0.1–1.0% by weight of the reaction mixture) was added. Then the reaction mixture was heated under reduced pressure (about 8 kPa) until it started boiling. The reduced pressure was maintained during the whole reaction. The mixture was allowed to boil at the lower temperature (50°–110° C. for 1 to 7 hours and at the higher temperature (110°–160° C.) for 1 to 10 hours. The progress of the reaction was followed by thin layer chromatography and quantitative IR spectrophotometry. At the end of the reaction the product mixture was neutralized and washed with an aqueous acid, filtrated and washed with water. Drying was performed with sodium sulphate. A liquid chromatogram and an IR spectrum were run from the final product. The yield was 92% of the theoretical yield.

EXAMPLE 5
Preparation of a methyl ester of tall oil

Tall oil (0.3 moles) was weighed into a three-necked flask provided with a thermometer, water separator and a cooler and a stirring device. Stirring was started and methanol (2.0 moles) was added. The reaction mixture was heated to 60° C. and the acid catalyst used (0.3% by weight) was added. Stirring was continued for six hours. The progress of the reaction was followed by thin layer chromatography and by the amount of water created. The reaction mixture was washed with alkaline water and dried with sodium sulphate. The mixture was filtrated and analyzed by liquid chromatography. Tall oil ester content was 97%.

EXAMPLE 6
Preparation of a synthetic ester from rapeseed oil methyl ester

The methyl ester of rapeseed oil (0.65 moles) was weighed into a three-necked flask provided with a thermometer, a cooler, a stirring device and a reduced pressure generator. Reduced pressure was drawn to the equipment, and the weighed rapeseed oil methyl ester was heated to 60°–120° C., after which pentaerythritol (PE, 0.19 moles) was added in small proportions with proper sting. After the alcohol was well mixed, sodium hydroxide used as a catalyst was added (0.1–1.0% by weight of the reaction mixture). Then the reaction mixture was heated under reduced pressure (about 8 kPa) and at a temperature of 80°–160° C. until it started boiling. The mixture was allowed to boil for about 5 to 10 hours. The progress of the reaction was followed by thin layer chromatography and quantitative IR spectrum. At the end of the reaction the product mixture was neutralized and washed with an aqueous acid, filtrated and washed with water. Drying was performed with anhydrous sodium sulfate. A liquid chromatogram and an IR spectrum were run of the final product. The yield was 87.5% of the theoretical.

EXAMPLE 7

Preparation of a hydraulic oil from a synthetic rapeseed oil ester and comparison of hydraulic oils The raw material used was the synthetic rapeseed oil ester obtained in Example 2. Said ester was mixed at a certain temperature with additives to obtain a hydraulic oil having the following composition:

| The synthetic ester from Example 2 | 90–98% by weight |
|---|---|
| Oxidation inhibitor | 0.1–2.5% by weight |
| Pour point depresser | 0–5.0% by weight |
| Antiwear agent | 0.1–2.0% by weight |
| Antifoam agent | 0–0.5% by weight |

The technical properties studied of this ester containing additives were wear, friction, oxidation, low temperature properties and corrosion.

Wear and friction were studied with a four ball test (ASTMD 2783, IP 239) wherein wear with respect to loading or the extreme loading where the lubrication still works, are measured. Oxidative properties were studied with an oxygen bomb test (ASTMD 925) and with the oxidation test DIN 51586 where the change of viscosity at 40° C. was monitored. In a corrosion test (Cincinnati-Milacron test) the aging of the oil as well as copper and steel corrosion were studied. In said test, the change of the total acid number (TAN) and viscosity, the weight change of the copper and steel rods used as oxidation catalysts in the test procedure and the formation of a precipitate under the test conditions are measured. Furthermore, the pour point which illustrates the low temperature properties of an oil was analyzed, i.e. the temperature where the oil is still fluid.

The corresponding properties were examined also from hydraulic oils based on rapeseed oil and hydraulic oils based on commercial synthetic esters. All the hydraulic oils were supplemented with the same additives as the hydraulic oil based on the ester prepared by the process of the invention. The results are shown in Table 1.

TABLE 1

Comparison of the properties of hydraulic oils. A = hydraulic oil with the ester prepared by the process of the invention as raw material, viscosity grade 32; B1 and B2 = hydraulic oils with commercial synthetic ester as raw materials, viscosity grades 46 and 68; C = commercial hydraulic oil based on rapeseed oil, viscosity grade 32.

|  | A | B1 | B2 | C |
|---|---|---|---|---|
| Four ball test |  |  |  |  |
| extreme loading, N | 2000 | 3000 | 2500 | 2000 |
| wearing, mm | 0.4 | 0.46 | 0.41 | 0.64 |
| Oxygen bomb test ASTDM D445, psi | 42 | 39 | 29 | 30 |
| Oxidation inhibition test DIN 51586, viscosity change, % | 12.4 | 20.3 | 24.1 | 28.8 |
| Cincinnati-Milacron test |  |  |  |  |
| TAN mg KOH/g |  |  |  |  |
| before | 1.39 | 1.39 | 1.40 | 1.72 |

TABLE 1-continued

Comparison of the properties of hydraulic oils. A = hydraulic oil with the ester prepared by the process of the invention as raw material, viscosity grade 32; B1 and B2 = hydraulic oils with commercial synthetic ester as raw materials, viscosity grades 46 and 68; C = commercial hydraulic oil based on rapeseed oil, viscosity grade 32.

|  | A | B1 | B2 | C |
|---|---|---|---|---|
| after | 1.56 | 3.71 | 2.41 | 0.61 |
| TAN | 0.17 | 2.32 | 1.01 | 1.11 |
| viscosity change, % | 19.1 | 16.9 | 6.2 | 8.2 |
| total precipitate, mg/100 ml | 1.1 | 17.0 | 28.8 | 4.4 |
| weight change of Cu rod, mg | 1.7 | −16.9 | 0 | −0.5 |
| weight change of steel rod, mg | −0.3 | 0.4 | 1.2 | −0.5 |
| Pour point, °C. | −41 | −36 | −39 | −39 |

From the results it can be seen that as regards oxidative and low temperature properties, the hydraulic oil based on the ester prepared by the process according to the invention is better than the commercial hydraulic oil based on rapeseed oil. The ester prepared by the process according to the invention and the corresponding commercial esters are equal with respect to oxidative and low temperature properties. From the Cincinnati-Milacron test it can be seen that the change of total acid number (TAN) is clearly lowest with the ester of the invention. The increase in viscosity at 40° C. is almost of the same order with all, as well as the weight change of copper and steel rods. Thus no corrosion is observed with any of the tested hydraulic oils under the test conditions used. The results of the oxygen bomb test are equal, as well as the results of the test according to DIN 51586 and the four ball test. Thus the wear and friction properties are equally good.

I claim:

1. A process for preparing a synthetic ester from a vegetable oil, comprising transesterifying said vegetable oil by reacting it with a lower alkanol to form a mixture of lower alkyl esters of fatty acids, transesterifying said mixture of lower alkyl esters of fatty acids in a second transesterification reaction by reacting said mixture with a no beta hydrogen polyol of the formula

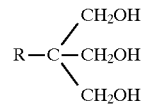

wherein R is a $C_1$–$C_6$ alkyl group or a —$CH_2OH$ group, and wherein said second transesterification is carried out in two stages, with a reaction temperature of from 50° to 100° C. in the first stage and with a reaction temperature of from 110° to 160° C. in the second stage and being higher than the temperature of said first stage.

2. The process according to claim 1, wherein the vegetable oil is selected from the group consisting of rapeseed oil, rape oil, tall oil and soybean oil.

3. The process according to claim 1, wherein the lower alkanol is a $C_1$–$C_4$ alkanol.

4. The process according to claim 1, wherein the fatty acid lower alkyl ester is a methyl ester of a fatty acid.

5. The process according to claim 1, wherein the no beta hydrogen alcohol is selected from the group consisting of trimethylol ethane, trimethylol propane, trimethylol butane and pentaerythritol.

6. The process according to claim 1, wherein the second transesterification reaction is carried out under reduced pressure in the presence of a catalyst.

7. The process of claim 6 wherein the no beta hydrogen polyol and the mixture of esters are reacted with each other in a molar ratio of from about 1:2 to about 1:5.

8. The process according to claim 1, wherein the no beta hydrogen polyol and the mixture of esters are reacted with each other in a molar ratio of from about 1:2 to about 1:5.

9. The process according to claim 8 wherein said molar ratio is about 1:3.5.

10. The process according to claim 1 wherein said lower alkanol is methanol or ethanol.

11. The process of claim 1 wherein the reaction temperature in the first stage of said second transesterification is from 85° to 100° C.

\* \* \* \* \*